United States Patent
Rossi-Montero et al.

(10) Patent No.: US 6,465,004 B1
(45) Date of Patent: Oct. 15, 2002

(54) SOLUBILITY ENHANCEMENT OF DRUGS IN TRANSDERMAL DRUG DELIVERY SYSTEMS AND METHODS OF USE

(75) Inventors: Sylvia Rossi-Montero, Miami, FL (US); Juan Mantelle, Miami, FL (US); David Kanios, Miami, FL (US); David Houze, Coconut Grove, FL (US)

(73) Assignee: Noven Pharmaceuticals, Inc., Miami, FL (US)

(*) Notice: Subject to any disclaimer, the term of this patent is extended or adjusted under 35 U.S.C. 154(b) by 0 days.

(21) Appl. No.: 09/586,906

(22) Filed: Jun. 5, 2000

Related U.S. Application Data (60) Provisional application No. 60/137,827, filed on Jun. 5, 1999.

(51) Int. Cl.[7] ............................ A61F 13/02; A61L 15/16
(52) U.S. Cl. ................................... 424/448; 424/449
(58) Field of Search .......................... 424/449, 448, 424/443

(56) References Cited

U.S. PATENT DOCUMENTS

| | | | |
|---|---|---|---|
| 4,668,232 A | | 5/1987 | Cordes et al. |
| 4,883,669 A | * | 11/1989 | Chien et al. |
| 4,900,554 A | * | 2/1990 | Yanagibashi et al. |
| 4,994,267 A | | 2/1991 | Sablotsky |
| 5,028,435 A | * | 7/1991 | Katz et al. |
| 5,120,546 A | * | 6/1992 | Hansen et al. |
| 5,232,702 A | | 8/1993 | Pfister et al. |
| 5,446,070 A | | 8/1995 | Mantelle |
| 5,474,783 A | | 12/1995 | Miranda et al. |
| 5,523,095 A | | 6/1996 | Wilson et al. |
| 5,589,498 A | | 12/1996 | Mohr et al. |
| 5,656,286 A | | 8/1997 | Miranda et al. |
| 5,662,923 A | * | 9/1997 | Roreger |
| 5,716,609 A | | 2/1998 | Jain et al. |
| 5,810,786 A | | 9/1998 | Jackson et al. |
| 5,885,612 A | | 3/1999 | Meconi et al. |
| 5,906,814 A | | 5/1999 | Epstein |
| 5,906,830 A | | 5/1999 | Farinas et al. |
| 5,968,542 A | * | 10/1999 | Tipton |
| 6,024,974 A | * | 2/2000 | Li |
| 6,231,885 B1 | * | 5/2001 | Carrara |

FOREIGN PATENT DOCUMENTS

| | | |
|---|---|---|
| EP | 156 080 A1 | 10/1985 |
| EP | 262 422 A1 | 4/1998 |
| EP | 913 158 A1 | 5/1999 |
| WO | WO92/15289 A1 | 9/1992 |
| WO | WO96/00072 A1 | 1/1996 |
| WO | WO98/39042 A1 | 9/1998 |
| WO | WO99/15156 A1 | 4/1999 |
| WO | PCT/US00/15538 | 12/2000 |

OTHER PUBLICATIONS

Eastman, Eastman Cellulose Esters for Pharmaceutical Drug Delivery, Publication EFC–223C, Oct. 1997, Eastman Chemical Co., Kingsport, Tennessee.*

John Wiley & Sons, Inc., Kirk–Othmer, "Cellulose Acetate and Triacetate Fibers/Cellulose Derivatives, Esters," pp. 82–129, 1979, *Encyclopedia of Chemical Technology*, 3rd Ed., vol. 5.

Eastman, *Eastman Cellulose Esters for Pharmaceutical Drug Delivery*, Oct. 1997, Publ. EFC–223C, Eastman Chemical Co., Kingsport, Tennessee.

* cited by examiner

*Primary Examiner*—Thurman K. Page
*Assistant Examiner*—Isis Ghali
(74) *Attorney, Agent, or Firm*—Jay G. Kolman (57) ABSTRACT

A composition and method for the continuous and controlled transdermal delivery of an active agent comprising a pharmaceutically acceptable active agent carrier and cellulose derivative which provides a solubilizing and stabilizing effect on the active agents incorporated therein.

14 Claims, 2 Drawing Sheets

Fig. 2

Flux Comparison of Cellulose Acetate Butyrates and PVP

SOLUBILITY ENHANCEMENT OF DRUGS IN TRANSDERMAL DRUG DELIVERY SYSTEMS AND METHODS OF USE

This application claims benefit of provisional No. 60/137,827 filed Jun. 5, 1999.

BACKGROUND OF THE INVENTION

This invention relates generally to transdermal drug delivery systems, and more particularly, to pressure-sensitive adhesive compositions for continuous and controlled delivery of active agents over a prolonged period of time that incorporate a cellulose derivative, and in particular esterified or acylated cellulose, to stabilize the concentration of the active agent in the composition and to inhibit crystal formation of the active agent.

The use of transdermal drug delivery systems as a means to topically administer an active agent is well known. Such systems incorporate the active agent into a carrier composition, such as a polymeric and/or pressure-sensitive adhesive composition, from which the active agent is delivered through the skin or mucosa of the user.

In general, transdermal drug delivery systems are either reservoir-type or matrix-type. Both types of systems include a backing layer that forms the protective outer surface of the finished transdermal device and which is exposed to the environment during use, and a release liner or protective layer that forms the inner surface and which covers the adhesive means for affixing the device to the skin or mucosa of a user. The release liner or protective layer is removed prior to application, exposing the adhesive means, which is typically a pressure-sensitive adhesive. The active agent is located between the release liner and backing layer, usually solubilized or dispersed in a solvent or carrier composition.

In a reservoir-type device, the active agent, typically in fluid or gel form, is isolated from the adhesive means used to affix the device to the user. Traditionally, a reservoir system referred to a device having a pocket or "reservoir" which served to hold the active agent and which was formed in or by the backing layer itself. A peripheral adhesive layer was then used to affix the device to the user. While such devices are still in use today, the term reservoir has become known as a device which employs one or more permeable layers, such as rate controlling membranes and drug permeable adhesives layers, laminated over the reservoir (which is typically nothing more than another layer containing the drug in a carrier composition), in order to more effectively control the delivery rate of the active agent and attachment of the device to the user.

A matrix-type device generally comprises the active agent solubilized or dispersed in an adhesive carrier composition, typically a pressure-sensitive adhesive or bioadhesive, which functions as both the drug carrier and the adhesive means of applying the system to the skin or mucosa. Such devices are described, for example, in U.S. Pat. Nos. 4,994,267, 5,446,070, 5,474,783 and 5,656,286, all of which are assigned to Noven Pharmaceuticals, Inc., Miami, Fla.

A particular advantage over other forms of drug delivery, such as oral administration, is that the transdermal system can provide a continuous and controlled release of the active agent over a prolonged period of time so that the resulting blood levels remain constant.

It has been shown that the degree of saturation and solubility of the active agent in the carrier composition are determining factors in controlling delivery of the active agent from the transdermal system. Since only solubilized active agent is available for delivery out of the transdermal system, the carrier composition must not promote crystal growth or formation, especially during storage of the system prior to use. Generally, active agents have been found to be readily soluble in acrylic polymers. However, in order to deliver a therapeutically effective amount to the system's user, and to also achieve the desired adhesive strength required for topical application in a matrix-type system, additional polymers and ingredients are often added to the carrier composition (for example, incorporating a rubber, polysiloxane or polyvinylpyrrolidone polymer). Such additional polymers and ingredients can affect the recrystallization of the active agent in the carrier composition. The tendency for crystal formation or growth is known, for example, in the case of steroid hormones.

Formulation of transdermal systems is further frequently hampered by poor solubility of certain active agents in the carrier composition, which in turn also severely limits its therapeutic application. This formulating aspect is particularly difficult in matrix-type systems because the carrier composition has to be optimized not only for the desired active agents but also for the carrier's pressure-sensitive adhesive properties. While using low concentrations in order to incorporate the active agent into the carrier may not deleteriously affect the carrier's adhesive properties, low active agent concentration can result in difficulties in achieving an acceptable delivery rate. Poor or inadequate solubility of the active agent further gives rise to crystal formation or growth.

Generally, concentrations of the active agent up to the saturation solubility, and even supersaturated (i.e., an amount of active agent at a concentration greater than the solubility of the active agent in the carrier composition at room temperature) are sought in order to increase or maximize delivery rates. Such systems also allow for continuous administration of the active drug in therapeutically effective amounts for prolonged periods of time, such as greater than 24 hours, and even up to 7 days or more. In such systems, however, the active agent can recrystallize unpredictably, especially during storage. This gives rise to stability problems.

Active agent that is present in crystalline form cannot be delivered through skin or mucosa. Inadequate delivery of the active agent in turn leads to blood levels falling below that which are therapeutically effective. Some transdermal systems rely upon both solubilized and crystalline forms of active agent to achieve the desired drug loading in the carrier composition. Although the drug crystals in such systems are intended to dissolve later, for example after application, such a process is unpredictable and interferes with achieving a controlled delivery rate, especially a zero-order kinetic delivery rate.

Failure to control crystal formation and growth can further interfere with the physical properties of the transdermal system. The presence of crystals, particularly in excessive amounts, can interfere with the carrier composition's adhesive properties in matrix-type transdermal systems. Furthermore, surface crystals can come into direct contact with the skin or mucosa and promote irritation. The presence of drug crystals is therefore generally undesirable.

SUMMARY OF THE INVENTION

It is therefore an object of this invention to provide a transdermal drug delivery system that can substantially suppress or prevent crystallization of active agents incorporated therein for the delivery of a therapeutically effective amount.

It is another object of this invention to provide a transdermal drug delivery system that can substantially suppress or prevent crystallization formation or growth of the active agents incorporated in a pressure-sensitive adhesive carrier composition while retaining good physical adhesive properties.

It is also an object of this invention to provide a transdermal drug delivery system that can incorporate saturated and supersaturated concentrations of the active agent, and deliver the same at a controlled and predictable release rate.

It is a further object of this invention to provide for transdermal drug delivery systems that can incorporate active agents that are insoluble or sparingly soluble in pressure-sensitive adhesives in amounts necessary to deliver a therapeutically effective amount without resulting in recrystallization of the active agent, and deliver the same at a controlled and predictable release rate.

It is still another object of this invention to provide a method for increasing the solubilizing and stabilizing of active agents in transdermal delivery systems.

It is additionally an object of this invention to provide a method for making a transdermal drug delivery system that achieves a substantially zero-order kinetic rate of drug delivery for a prolonged period of time without crystallization of the active agent therein.

DETAILED DESCRIPTION OF THE INVENTION

The foregoing and other objects are achieved by this invention which provides a transdermal drug delivery system wherein the use of a cellulose derivative provides a solubilizing and stabilizing effect on the active agents incorporated into the carrier composition.

The term "topical" or "topically" is used herein in its conventional. meaning as referring to direct contact with an anatomical site or surface area on a mammal including skin, teeth, nails and mucosa.

The term "mucosa" as used herein means any moist anatomical membrane or surface on a mammal such as oral, buccal, vaginal, rectal, nasal or ophthalmic surfaces.

The term "transdermal" as used herein means passage of an active agent into and/or through skin or mucosa for localized or systemic delivery.

The term "solubilized" is intended to mean that in the carrier composition there is an intimate dispersion or dissolution of the active agent at the crystalline, molecular or ionic level, such that crystals of the active agent cannot be detected using a microscope having a magnification of 25X. As such, the active agent is considered herein to be in "non-crystallized" form when in the compositions of the present invention.

As used herein, the term "flux" is defined as the absorption of the drug through the skin or mucosa, and is described by Fick's first law of diffusion:

$$J = -D \, (dCm/dx),$$

Where J is the flux in $g/cm^2/sec$, D is the diffusion coefficient of the drug through the skin or mucosa in $cm^2/sec$ and $Dcm/dx$ is the concentration gradient of the drug across the skin or mucosa.

The term "about", and the use of ranges in general whether or not qualified by the term about, means that the number comprehended is not limited to the exact number set forth herein, and is intended to refer to ranges substantially within the quoted range not departing from the scope of the invention.

The term "user" or "subject" is intended to include all warm-blooded mammals, preferably humans.

The phrase "substantially zero-order" as used herein means transdermal delivery of an active agent at a release rate which is approximately constant once steady state is attained, typically within 12 hours or less after topical application. While variability in blood levels of active agent are contemplated within the scope of this meaning once steady state release is attained, the depletion rate of active agent over the duration of use should typically not exceed about 20% to about 25%.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

The cellulose derivatives of the present invention preferably have at least 2 anhydroglucose rings and most preferably have from about 2 to about 5,000 anhydroglucose rings. In addition, the degree of substitution for acetyl per anhydroglucose unit of the cellulose derivative is preferably from about 0.1 to about 2.9, more preferably from about 0.1 to about 2.0, and optimally from about 0.1 to about 0.5. Moreover, the acetyl content is from about 2% to about 45% and more preferably from about 2% to about 30%.

In accordance with one aspect of the invention, an improved pressure-sensitive adhesive carrier composition which is suitable for controlled and continuous delivery of an active agent from a matrix-type transdermal system comprises one or more pressure-sensitive adhesives and an esterified or acylated cellulose.

Exemplary esterified or acylated cellulose derivatives suitable for use in practicing this invention include those which are substituted by one to three acetyl groups or by one or two acetyl groups and a further acyl radical other than acetyl, such as cellulose acetate dimethylamino acetate, cellulose acetate ethyl and methyl carbonate, cellulose acetate phthalate, cellulose acetate succinate, cellulose acetate chloroacetate, cellulose diacetate, cellulose triacetate, cellulose acetate ethyl oxalate, cellulose acetate methyl and butyl sulfonate, cellulose acetate octate, cellulose acetate laurate, cellulose acetate p-toluene sulfonate, cellulose acetate ethyl and methyl carbomate, cellulose acetate valerate, cellulose acetate maleate, and the like, and combinations and mixtures thereof.

Preferred cellulose esters are cellulose acetate, cellulose acetate propionate, cellulose acetate butyrate, cellulose acetate phthalate, cellulose propionate butyrate, and the like, and combinations and mixtures thereof. Such cellulose derivatives can be prepared by any known technique in the art (for example, see Kirk-Othmer, Encyclopedia of Chemical Technology, 3rd Edition, Vol. 5, John Wiley & Sons, New York, N.Y., 1979, p. 89–129; and Libscomb, A. G., Cellulose Acetate: Its Manufacture and Applications, Ernest Benn, Ltd. London, GB, 1933), or can be obtained commercially (for example, from Eastman Chemical Products, Inc., Kingsport, Tenn.).

The particularly preferred cellulose esters are those that do not exhibit pH-dependent solubility characteristics are insoluble in water and are soluble in the carrier material. Examples include cellulose acetate butyrates (CAB) and cellulose acetate propionates (CAP). Particularly preferred cellulose acetate butyrates are CAB-171-15PG, CAB-381-0.1, CAB-500-5, and CAB-553-0.4, which are all commercially available from Eastman Chemical Products, Inc., Kingsport, Tenn.). In the foregoing description, the first two digits indicate the approximate butyryl content at the triester stage, the third digit indicates the number of hydroxyl groups for each four anhydroglucose units, and the last digit(s) indicate the viscosity of the ester. CABs with higher butyryl content, such as greater than 30%, tend to be more effective in suppressing crystal formation.

Figure 2:
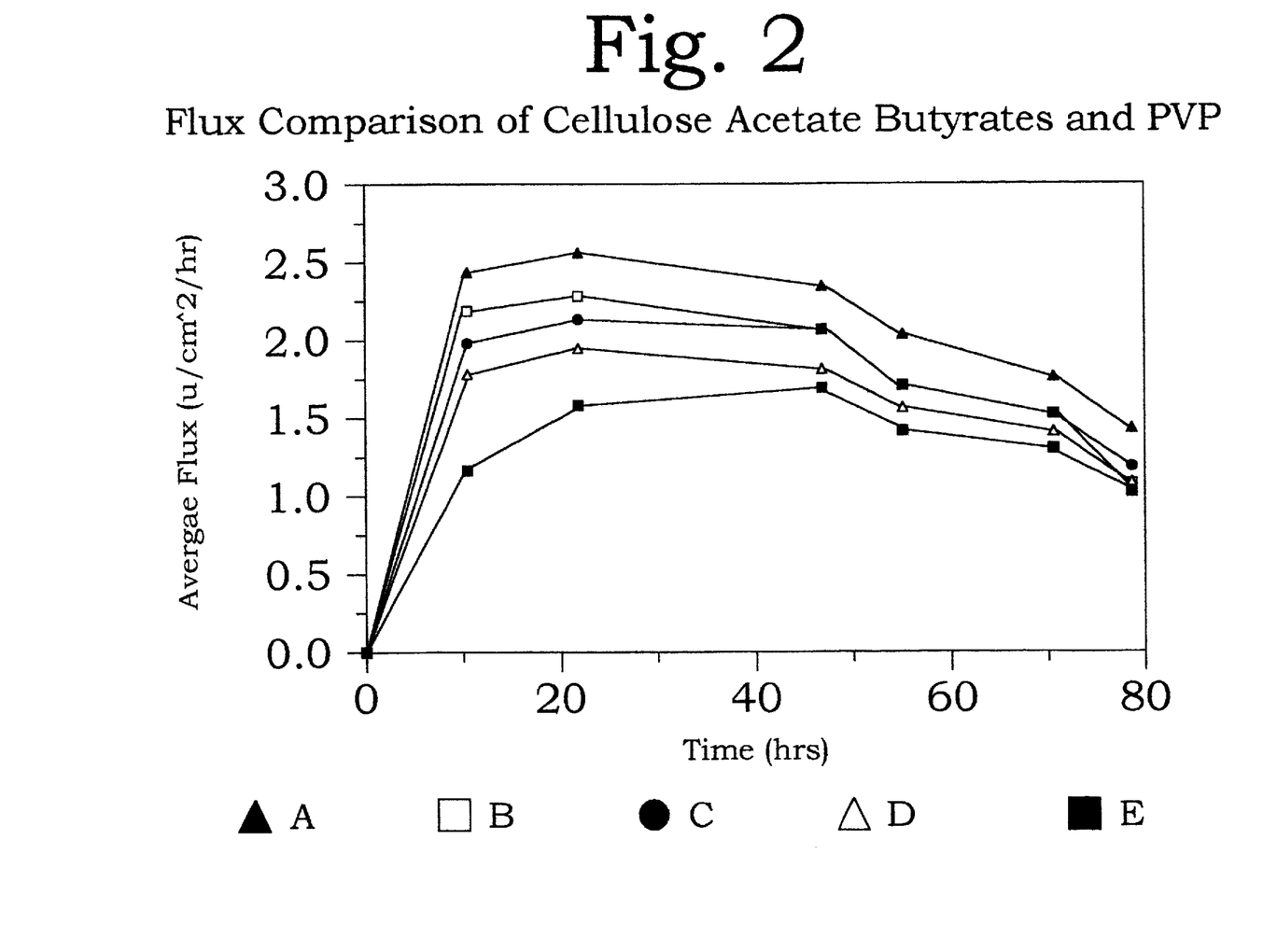
FIG. 2 is a graphical representation of the steady state flux rate of methyltestosterone through cadaver skin from pressure-sensitive adhesive carrier compositions of the present invention comprising cellulose esters as compared to a pressure-sensitive adhesive carrier composition comprising polyvinylpyrrolidone.

CABs are particularly suitable to suppress crystallization in pressure-sensitive adhesive carrier compositions containing steroidal hormones, such as methyltestosterone, and allow for the delivery of a desired dose continuously. FIG. 2 graphically demonstrates the in vitro flux results through cadaver skin from matrix-type transdermal systems comprising pressure-sensitive carrier compositions incorporating CABs and soluble polyvinylpyrrolidone (PVP). The use of soluble PVP as a drug crystallization inhibitor and solubility enhancer is known in the art.

Five formulations were prepared using the method of Example I to yield compositions having the ingredient concentrations, by weight based on the dry weight of the total carrier composition, set forth in TABLE I.

TABLE I

| INGREDIENT | WEIGHT % | | | | |
| --- | --- | --- | --- | --- | --- |
| | Ex. A | Ex. B | Ex. C | Ex. D | Ex. E |
| Polysiloxane Adhesive (BIO-PSA ® Q7-4502) | 50.9 | 50.9 | 50.9 | 50.9 | 42.9 |
| Polyacrylate Adhesive (DURO-TAK ® 87-2510) | 20.0 | 20.0 | 20.0 | 20.0 | 20.0 |
| CAB 381-0.1 | 10.0 | 7.0 | — | — | — |
| CAB 500-5 | — | 3.0 | — | 10.0 | — |
| CAB 553-0.4 | — | — | 10.0 | — | — |
| Soluble PVP (KOLLIDON ® 30)* | — | — | — | — | 20.0 |
| Oleyl Alcohol | 6.0 | 6.0 | 6.0 | 6.0 | 6.0 |
| Dipropylene Glycol | 8.0 | 8.0 | 8.0 | 8.0 | 8.0 |
| Estradiol | 1.1 | 1.1 | 1.1 | 1.1 | 1.1 |
| Methyltestosterone | 4.0 | 4.0 | 4.0 | 4.0 | 2.0 |

*(BASF AG, Ludwigshafen, Germany).

The particular soluble PVP was selected based on its respective solubility in similar volatile solvents and its similar molecular weight to the two CABs to which it was compared. As seen in FIG. 2, the carrier compositions containing CABs were able to incorporate twice as much drug and yield flux rates as much as 47% greater than the carrier composition containing the soluble PVP. In terms of drug crystallization, the soluble PVP concentration used in Example E, which is double the corresponding weight percent of CABs, was necessitated in order to suppress drug crystal growth. Moreover, large drug crystals were observed when using 20% soluble PVP (stored 25 days at room temperature and a relative humidity of 60–75%) with 4% methyltestosterone. It was therefore necessary to additionally halve the methyltestosterone weight percent (i.e., to 2%).

The amount and type of the esterified or acylated cellulose required in the practice of the invention will depend on the one or more additional polymeric materials and ingredients in the carrier composition, and on the amount and type of active agent. Generally, the amount to be used is an amount sufficient to deliver a therapeutically effective amount of the active agent at a substantially zero-order kinetic rate of delivery for a prolonged period of time (i.e., greater than 24 hours), and to substantially suppress or prevent recrystallization of the active agent during storage. Typically, the amount of the esterified or acylated cellulose to be used ranges from about 0.5% to about 50%, preferably from about 0.5% to 40%, and more preferably from about 2.5% to 30% by weight based on the dry weight of the total carrier composition.

As used herein, "therapeutically effective" means an amount of an active agent that is sufficient to achieve the desired local or systemic effect or result, such as to prevent, cure, diagnose, mitigate or treat a disease or condition, when applied topically over the duration of intended use. The amounts necessary are known in the literature or may be determined by methods known in the art, but typically range from about 0.1 mg to about 20,000 mg, and preferably from about 0.1 mg to about 1,000 mg, and most preferably from about 0.1 to about 500 mg per human adult or mammal of about 75 kg body weight per 24 hours.

The term "active agent" (and its equivalents "agent," "drug," "medicament" and "pharmaceutical") is intended to have the broadest meaning and includes at least one of any therapeutic, prophylactic, pharmacological or physiological active substance, cosmetic and personal care preparations, and mixtures thereof, which is delivered to a mammal to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. It should be noted that the active agents can be used singularly or in combinations and mixtures.

There is no limitation on the type of active agent that can be used in this invention. However, active agents that are solid at room temperature are preferred.

The active agents contained in the carrier composition can be in different forms depending on the solubility and release characteristics desired, for example as neutral molecules, components of molecular complexes, and pharmaceutically acceptable salts, free acids or bases, or quaternary salts of the same. Simple derivatives of the drugs such as pharmaceutically acceptable ethers, esters, amides and the like which have desirable retention and release characteristics but which are easily metabolized at body pH, and enzymes, pro-active forms, pro-drugs and the like, can also be employed.

Steroidal hormones and active agents that generally tend to be poorly soluble or insoluble in pressure-sensitive adhesive carrier compositions are preferred and include, for example, Estrogenically effective steroid hormones such as Colpormon, Conjugated Estrogens, Estradiol (17β- and α-)and its Esters (e.g., Acetate, Benzoate, Cypionate, Dipropionate Diacetate, Enanthate, Undecylate and Valerate), Estriol, Estrone, Ethinyl Estradiol, Equilenin, Equilin, Mestranol, Moxestrol, Myatrienediol, Quinestradiol and Quinestrol; Progestagenically effective steroid hormones such as Allylestrenol, Anagestone, Chlormadinone Acetate, Delmadinone Acetate, Demegestone, Desogestrel, 3-Keto Desogestrel, Dimethisterone, Dydrogesterone, Ethinylestrenol, Ethisterone, Ethynodiol (and Diacetate), Flurogestone Acetate, Gestodene, Gestonorone Caproate, Haloprogesterone, (17-Hydroxy- and 17-Acetate-)

16-Methylene-Progesterone, 17α-Hydroxyprogesterone (Acetate and Caproate), Levonorgestrel, Lynestrenol, Medrogestone, Medroxyprogesterone (and Acetate), Megestrol Acetate, Melengestrol, Norethindrone (Acetate and Enanthate), Norethisterone, Norethynodrel, Norgesterone, Norgestimate, Norgestrel, Norgestrienone, 19-Norprogesterone, Norvinisterone, Pentagestrone, Progesterone, Promegestone, Quingestrone and Trengestone; Androgenically effective steroid hormones such as Aldosterone, Androsterone, Boldenone, Cloxotestosterone, Dehydroepiandrosterone, Fluoxymesterone, Mestanolone, Mesterolone, Methandrostenolone, Methyltestosterone, 17α-Methyltesteosterone, 17α-Methyltestosterone 3-Cyclopentyl Enol Ether, Norethandrolone, Normethandrone, Oxandrolone, Oxymesterone, Oxymetholone, Prasterone, Stanlolone, Stanozolol, Testosterone (Acetate, Enanthate, Isobutyrate, Propionate and Undecanoate), Testosterone 17-Chloral Hemiacetal, Testosterone 17β-Cypionate and Tiomesterone.

Other specific drugs for which cellulose derivatives can be particularly usefully employed according to the invention include:

1. α-Adrenergic Agonist agents such as Phenylpropanolamine and Talipexole.
2. Analgesics and/or Anti-Migraine such as Acetaminophen, Acetylsalicylic Acid, Buprenorphine, Codeine, Fentanyl, Hydomorphone, Lisuride, Salicylic Acid derivatives, Sufentanil and Sumatriptan.
3. Anti-Allergic agents such as Amlexanox, Astemizole, Azelastine, Cromolyn, Fenpiprane, Ibudilast, Nedocromil, Oxatomide, Pentigetide, Repirinast, Tranilast and Traxanox.
4. Anesthetic agents such as Benzocaine, Bupivicaine, Cocaine, Dibucaine, Dyclonine, Etidocaine, Lidocaine, Mepivacaine, Prilocaine, Procaine and Tetracaine.
5. Anoretic agents such as Fenfluramine, Mazindol and Phentermine.
6. Anti-Bacterial (antibiotic) agents including Aminoglycosides, B-Lactams, Cephamycins, Macrolides, Penicillins, Polypeptides and Tetracyclines.
7. Anti-Cancer agents such as Aminolevulinic Acid, 5-Fluouracil, Methotrexate, Tamoxifen and Taxol.
8. Anti-Cholinergic agents such as Atropine, Eucatropine and Procyclidine.
9. Anti-Diabetic agents such as Glipizide, Glyburide, Glypinamide, Insulins, Repaglinide, Rosiglitazone and Troglitazone.
10. Anti-Emetic agents such as Acetylleucine Monoethanolamine, Alizapride, Benzquinamide, Bietanautine, Bromopride, Buclizine, Chlorpromazine, Clebopride, Cyclizine, Dimenhydrinate, Dipheniodol, Domperidone, Granisetron, Meclizine, Methalltal, Metoclopramide, Metopimazine, Nabilone, Ondansteron, Oxypendyl, Pipamazine, Piprinhydrinate, Prochlorperazine, Scopolamine, Tetrahydrocannabinols, Thiethylperazine, Thioproperzaine, Trimethobenzamide and Tropisetron.
11. Anti-Fungal agents such as Clortrimazole, Ketoconazole, Miconazole, Nystatin and Triacetin.
12. Antihistamine agents such as Tricyclics such as Ahistan, Etymemazine, Fenethazine, N-Hydroxyethylpromethazine Chloride, Isopromethazine, Mequitazine, Promethazine, Pyrathiazine, and Thiazinamium Methyl Sulfate, and Loratadine and Clobenzepam.
13. Anti-Hyperlipoproteinemic agents such as Atorvastatin, Cerivastatin, Lovastatin, Pravastatin and Simvastatin.
14. Anti-Hyperthyroid agents such as Methimazole.
15. Anti-Inflammatory and/or Corticoid agents such as Beclomethasone, Betamethasone (and Acetate, Diproprionate and Valerate), Corticosterone, Cortisone, Deoxycortocosterone (and Acetate), Dexamethasone, Diclofenac, Fenoprofen, Flucinolone (and Acetonide), Fludrocortisone, Fluocinonide, Flunisolide, Fluradrenolide, Flurbiprofen, Halcinonide, Hydrocortisone (and Acetate), Ibuprofen, Ibuproxam, Indoprofen, Ketoprofen, Ketorolac, Naproxen, Oxametacine, Oxyphenbutazone, Piroxicam, Prednisolone, Prednisone, Suprofen and Triamcinolone (and Acetonide).
16. Anti-Malarial agents such as Pyrimethamine.
17. Anti-Parkinson's and/or Anti-Alzhiemer's agents such as Biperiden, Bromocriptine, Cabergoline, 1-Hydroxy-Tacrine, Levodopa, Lisuride, Pergolide, Pramipexole, Quinpirole, Ropinirole, Rivastigmine, Physostigimine, Selegiline (Deprenyl and L-Deprenyl), Tacrine and Teruride.
18. Anti-Psychotic and/or Anti-Anxiety and/or Anti-Depressant agents such as Acetophenazine, Bromperidol, Chlorproethazine, Chlorpromazine, Clomipramine, Clozapine, Fluoxetine, Fluphenazine, Haloperidol, Loxapine, Mesoridazine, Molindone, Paroxetine, Perphenazine, Piperacetazine, Sertraline, Thiopropazate, Thioridazine, Thiothixene, Trifluoperazine, Triflupromazine and Venlafaxine.
19. Anti-Ulcerative agents such as Enprostil and Misoprostol.
20. Anti-Viral agents such as Acyclovir, Rimantadine and Vidarabine.
21. Anxiolytic agents such as Azapirones such as Buspirone and Ipsapirone, Benzodiazepines such as Alprazolam, Chlordiazepoxide, Clonazepam, Clorazepate, Diazepam, Flurazepam, Halazepam, Lorazepam, Oxazepam, Oxazolam, Prazepam and Triazolam.
22. B-Adrenergic agonist agents such as Albuterol, Carbuterol, Fenoterol, Metaproterenol, Mirtazapine, Rimiterol, Quinterenol, Salmefamol, Soterenol, Tratoquinol, Terbutaline and Terbuterol.
23. Bronchodilators such as Ephedrine derivatives including Epiniphrine and Isoproterenol, Albuterol, Salbutanol, Clenbuterol and Theophylline.
24. Cardioactive agents such as Atenolol, Benzydroflumethiazide, Bendroflumethiazide, Calcitonin, Captopril, Chlorothiazide, Clonidine, Clopamide, Dobutamine, Dopamine, Diltiazem, Enalapril, Enalaprilat, Gallopamil, Indomethacin, Isosorbide (Dinitrate and Mononitrate), Monoxidil, Nicardipine, Nifedipine, Nitroglycerin, Papaverine, Prazosin, Procainamide, Propranolol, Prostaglandin ($E_1$ and $E_2$), Quinidine Sulfate, Timolol, and Verapamil.
25. Central Nervous System stimulants and agents such as Dextroamphetamine, Methylphenidate (and each Enantiomer and Free Base Form) and Nicotine.
26. Cholinergic agents such as Acetylcholine, Arecoline, Bethanechol, Carbachol, Choline, Methacoline, Muscarine and Pilocarpine.
27. Muscle relaxants such as Baclofen.

28. Narcotic antagonist agents such Nalmfene and Naloxone.

The amount of active agent to be incorporated in the carrier composition will vary depending on the particular active agent, the desired therapeutic effect, and the time span for which the transdermal system is to provide therapy. Normally, the amount of active agent in the transdermal system can vary from about 0.1% to about 50%, and preferably from about 0.1% to about 30% by weight based on the dry weight of the total carrier composition. For lower dose concentrations permitted by this invention, such as with steroidal hormones, the preferred amount is from about 0.1% to about 10%.

While not essential, it is preferred that the androgenic hormones be incorporated near, at or above saturation with respect to its concentration in the carrier composition.

The term "carrier" as used herein refers to any non-aqueous material known in the art as suitable for transdermal drug delivery administration, and includes any polymeric material into which an active agent may be solubilized in combination or admixture with the other ingredients of the composition. The polymeric materials preferably comprise adhesives and, in particular, pressure-sensitive adhesives. The carrier material is typically used in an amount of about 10% to about 90%, and preferably from about 10% to about 75%, by weight based on the dry weight of the total carrier composition.

The term "carrier composition" may also refer to enhancers, solvents, co-solvents and other types of addictives useful for facilitating transdermal drug delivery. An "adhesive" as used herein means any natural or synthetic substance that is capable of surface attachment to the topical site of the transdermal drug delivery system.

CABs have been found to be highly effective in preventing crystallization of active agents in pressure-sensitive adhesive carrier compositions. An adhesive is a pressure-sensitive adhesive within the meaning of the term as used herein if it has the properties of a pressure-sensitive adhesive per se or if it functions as a pressure-sensitive adhesive by admixture with tackifiers, plasticizers, cross-linking agents or other additives.

Pressure-sensitive adhesives include all of the non-toxic natural and synthetic polymers known or suitable for use in transdermal systems as adhesives, such as polyacrylates, polysiloxanes, silicones, rubbers, gums, polyisobutylenes, polyvinylethers, polyurethanes, styrene block copolymers, styrene/butadiene polymers, polyether block amide copolymers, ethylene/vinyl acetate copolymers, and vinyl acetate based adhesives.

The pressure-sensitive adhesives particularly useful in practicing this invention include polyacrylates of one or more monomers of acrylic acids or other copolymerizable monomers. Polyacrylate adhesives also include polymers of alkyl acrylates and/or methacrylates and/or copolymerizable secondary monomers, or monomers with functional groups, and in particular hydroxy functional groups. The term "polyacrylate" is intended to be used interchangeably with the terms acrylic, acrylate and polyacrylic as used herein and as known in the art. Suitable pressure-sensitive acrylic adhesives are commercially available and include those sold under the trademark DURO-TAK® by National Starch and Chemical Company, Bridgewater, N.J., and GELVA® Multipolymer Solution by Solutia, Inc., St. Louis, Mo.

The pressure-sensitive adhesives useful in practicing the invention include solvent-based, hot melt and grafted adhesives, and may be used alone or in combinations, mixtures or blends. Particularly preferred blends include blends of polyacrylates and polysiloxanes.

The carrier compositions of the present invention can also contain one or more solvents and/or co-solvents. Such solvents and/or co-solvents are those known in the art, and are non-toxic, pharmaceutically acceptable substances, preferably liquids, which do not substantially negatively affect the adhesive properties or the solubility of the active agents at the concentrations used. The solvent and/or co-solvent can be for the active agent or for the carrier materials, or both.

Suitable solvents include volatile liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate isobutyl isobutyrate, hexyl acetate, 2-ethylhexyl acetate or butyl acetate); and combinations and mixtures thereof.

Suitable co-solvents include polyhydric alcohols, which include glycols, triols and polyols such as ethylene glycol, diethylene glycol, propylene glycol, dipropylene glycol, trimethylene glycol, butylene glycol, polyethylene glycol, hexylene glycol, polyoxethylene, glycerin, trimethylpropane, sorbitol, polyvinylpyrrolidone, and the like.

Further suitable co-solvents include glycol ethers such as ethylene glycol monoethyl ether, glycol esters, glycol ether esters such as ethylene glycol monoethyl ether acetate and ethylene glycol diacetate; saturated and unsaturated fatty acids, mineral oil, silicone fluid, lecithin, retinol derivatives and the like, and ethers, esters and alcohols of fatty acids.

Although the exact amount of co-solvents that may be used in the carrier composition depends on the nature and amount of the other ingredients, such amount typically ranges from about 0.1% to about 40%, and preferably from about 0.1% to about 30% by weight, and more preferably from about 1% to about 20%, by weight based on the dry weight of the total carrier composition.

In certain embodiments of the invention, an enhancer is incorporated into the carrier composition. The term "enhancers" as used herein refers to substances used to increase permeability and/or accelerate the delivery of an active agent through the skin or mucosa, and include monhydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearly) including polyoxyethylene (4) lauryl ether, polyoxyethylene (2) oleyl ether and polyoxyethylene (10) oleyl ether commercially available under the trademark BRIJ® 30, 93 and 97 from ICI Americas, Inc., and BRIJ® 35, 52, 56, 58, 72, 76, 78, 92, 96, 700 and 721; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered and esters of sorbitol and sorbitol anhydride such as polysorbate 20 commercially available under the trademark Tween® 20 from ICI Americas, Inc., as well as other polysorbates such as 21, 40,60, 61, 65, 80, 81, and 85. Other suitable enhancers include oleic and linoleic acids, triacetin, ascorbic acid, panthenol, butylated hydroxytoluene, tocopherol, tocopherol acetate, tocopheryl linoleate. If enhancers are incorporated into the carrier composition, the amount typically ranges up to about 30%, and preferably from about 0.1% to about 15%, by weight based on the dry weight of the total carrier composition.

In addition to enhancers, there may also be incorporated various pharmaceutically acceptable additives and excipients available to those skilled in the art. These additives include tackifying agents such as aliphatic hydrocarbons, mixed aliphatic and aromatic hydrocarbons, aromatic hydrocarbons, substituted aromatic hydrocarbons, hydrogenated esters, polyterpenes, silicone fluid, mineral oil and hydrogenated wood rosins. Additional additives include binders such as lecithin which "bind" the other ingredients, or rheological agents (thickeners) containing silicone such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, for purposes of enhancing the uniform consistency or continuous phase of the final composition. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the carrier composition. Such additives or excipients are typically used in amounts up to 25%, and preferably from about 0.1% to about 10%, by weight based on the dry weight of the total carrier composition.

The carrier compositions according to the present invention can be prepared by first mixing appropriate amounts of the cellulose derivative(s) in volatile polar and/or non-polar organic liquids such as those previously described as suitable volatile solvents. Appropriate amounts of active agent (s) are then added to the mixture together with appropriate amounts of pressure-sensitive adhesive(s), solvent(s) and/or co-solvent(s), with or without enhancer(s), and thoroughly mixed. The mixture of the carrier composition is next formed into a film at ambient temperature, preferably by coating or casting at a controlled specified thickness onto a flexible sheet material, such as a release liner, followed by evaporation of the volatile solvents at elevated temperatures (e.g., by passing through an oven). The non-volatile or higher boiling point solvents and/or co-solvents, such as the polyols, used in the carrier composition remain therein. The carrier composition has been coated or cast on the flexible sheet material, is then laminated to another flexible sheet material preferably a backing layer. Appropriate size and shape individual transdermal drug delivery systems are cut and then packaged (e.g., pouched).

The order of steps, the amount of the ingredients, and the amount and time of mixing may be important process variables which will depend on the specific polymers, active agents, solvents and/or co-solvents, enhancers and additives and excipients used in the composition. These factors can be adjusted by those skilled in the art, while keeping in mind the objects of achieving a solubilized active agent and providing a uniform product that will also give desirable results.

Further details and examples of pressure-sensitive adhesives, enhancers, solvents, co-solvents, and other additives, as well as transdermal systems generally, suitable in practicing the invention are described in U.S. Pat. Nos. 5,474,787, 5,656,286 and 60/115,987, all of which are assigned to Noven Pharmaceuticals, Inc. and incorporated herein by reference.

Figure 1:
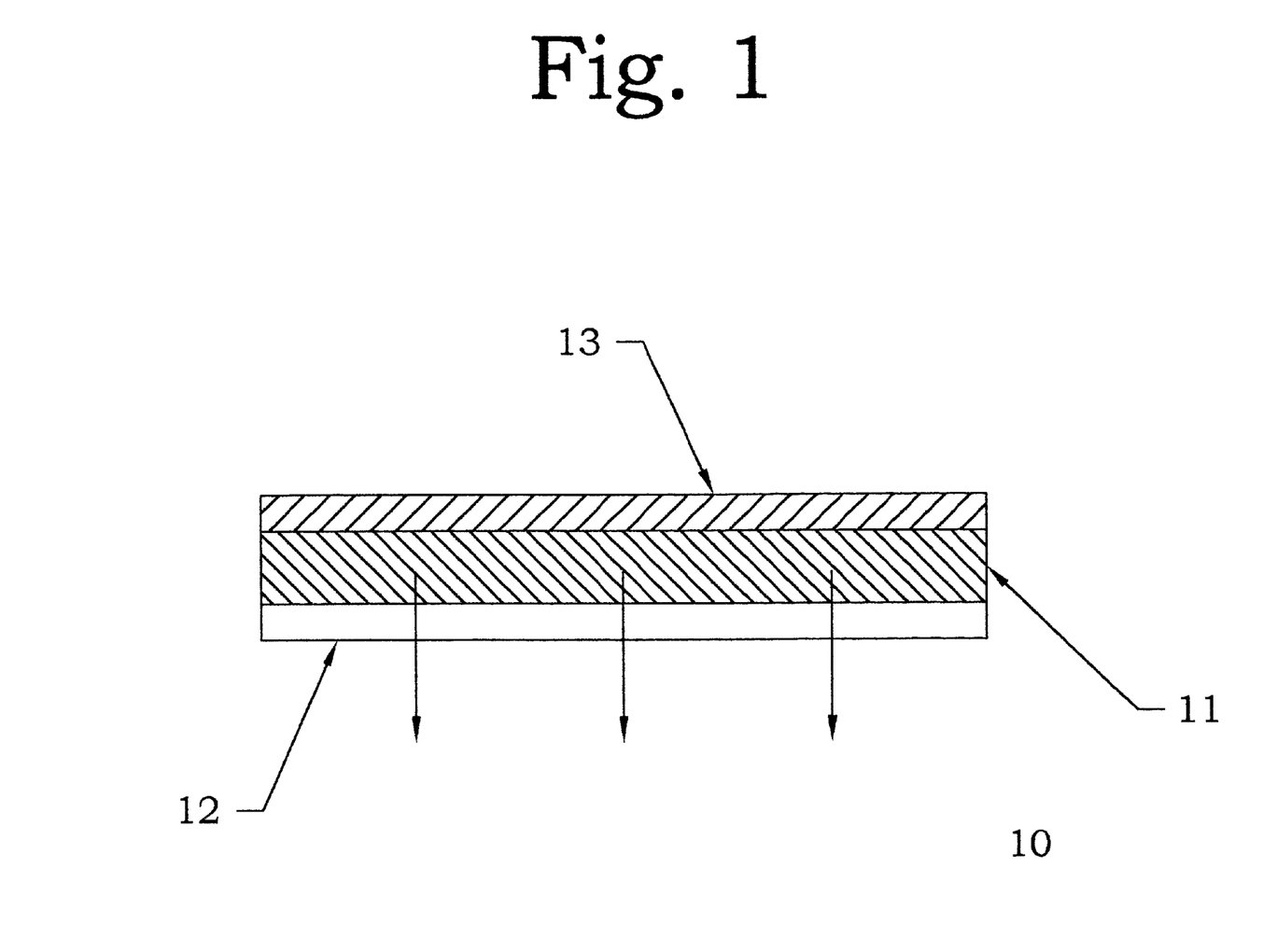
FIG. 1 is a schematic illustration of a matrix-type transdermal drug delivery system of the present invention.

A particularly preferred structure for the transdermal drug delivery system useful in practicing this invention is a matrix-type system. Reference to FIG. 1 shows a matrix-type transdermal drug delivery system 10 comprising a pressure-sensitive adhesive carrier composition layer 11, a release liner 12, and a backing layer 13. Removal of the release liner 12 exposes the pressure-sensitive adhesive carrier composition for topical application to the user.

It is understood that a reservoir-type system, provided with a separate pressure-sensitive adhesive layer or adhesive means of attachment, is contemplated in practicing the invention and may well be of advantage in certain cases. The reservoir-type system may further consist of one or more layers or membranes. Regardless of the type of transdermal system used to practice the invention, the carrier composition is preferably non-aqueous (i.e., substantially free of water).

EXAMPLES

The above description and following specific examples are hereby illustrative of pharmaceutically acceptable active agent carrier compositions and transdermal drug delivery systems, and methods of making same, within the contemplation of the invention. The description and examples are in no way intended to be, or should be considered, limiting of the scope of the invention. And while efforts have been made to ensure accuracy with respect to numbers used (such as amounts and temperatures), some experimental error and deviation should be accounted for and/or allowed.

Example 1

An estradiol/methyltestosterone pressure-sensitive adhesive mixture was prepared by combining 4.0 parts of methyltestosterone and 1.1 parts of estradiol in a solution of 42.3 parts of CAB-381-0.1 with 38.0 parts each of isopropyl alcohol and ethyl acetate. Then 76.5 parts of a polysiloxane adhesive (BIO-PSA® Q7-4502, a silicone in ethyl acetate; Dow Corning Corporation, Medical Products, Midland, Mich.), 48.8 parts of a polyacrylate adhesive (DURO-TAK® 87-2510, an acrylate copolymer in ethyl acetate and hexane; National Starch and Chemical Corporation, Bridgewater, N.J.), 8.0 parts of dipropylene glycol and 6.0 parts of oleyl alcohol were added and thoroughly mixed in an appropriate container until the mixture was completely homogeneous. The resulting composition had the ingredient concentrations on a dry weight percent basis (i.e., after evaporation of volatile solvents) as shown below.

| INGREDIENT | WEIGHT % |
|---|---|
| Polysiloxane Adhesive (BIO-PSA ® Q7-4502) | 45.9 |

-continued

| INGREDIENT | WEIGHT % |
|---|---|
| Polyacrylate Adhesive (DURO-TAK ® 87-2510) | 20.0 |
| Cellulose Acetate Butyrate CAB 381-0.1) | 15.0 |
| Dipropylene Glycol | 8.0 |
| Estradiol | 1.1 |
| Methyltestosterone | 4.0 |
|  | 100.0 |

Examples 2–5

In the following examples, the method of Example 1 was used with the appropriate amounts of starting materials to yield compositions having the following ingredient concentrations set forth in tabular form in TABLE II. Example 2 is presented as a control formulation to demonstrate the effect that CABs have on reducing drug crystallization formation.

TABLE II

| INGREDIENT | WEIGHT % | | | |
|---|---|---|---|---|
|  | Ex. 2 | Ex. 3 | Ex. 4 | Ex. 5 |
| Polysiloxane Adhesive (BIO-PSA ® Q7-4502) | 60.9 | — | 45.9 | 45.9 |
| Polysiloxane Adhesive* (BIO-PSA ® Q7-4302) | — | 49.9 | — | — |
| Polyacrylate Adhesive (DURO-TAK ® 87-2510) | 20.0 | 20.0 | 20.0 | 20.0 |
| CAB 171-15 PG | — | 15.0 | — | — |
| CAB 500-5 | — | — | 15.0 | — |
| CAB 553-0.4 | — | — | — | 15.0 |
| Oleyl Alcohol | 6.0 | — | 6.0 | 6.0 |
| Dipropylene Glycol | 5.0 | 10.0 | 8.0 | 8.0 |
| Estradiol | 1.1 | 1.1 | 1.1 | 1.1 |
| Methyltestosterone | 4.0 | 4.0 | 4.0 | 4.0 |

*Methylated trimethylated silica in ethyl acetate

The rate of crystallization formation of the two active ingredients in the matrix-type systems of Examples 1–5 was compared and the incidence of crystal formation set forth in tabular form in TABLE III. Comparison of the examples after 25 days, maintained at 25° C.±5° C. and a relative humidity of 65–70%, demonstrates the distinct reduction in the number of crystals in the adhesive carrier composition.

TABLE III

Effect of CABs on crystal formation

| Example | # of crystals in patch* |
|---|---|
| 1 | 23 ± 6 |
| 2 | >500 |
| 3 | 30 ± 6 |
| 4 | 2 ± 1 |
| 5 | 2 ± 1 |

*Approximate number of crystals visible in a 10 cm2 patch.

What is claimed is:

1. A transdermal drug delivery system comprising
   a pharmaceutically acceptable non-aqueous pressure-sensitive adhesive carrier composition comprising a blend of,
   (i) one or more adhesives selected from the group consisting of polyacrylates, polysiloxanes, silicones, rubbers, gums, polyisobutylenes, polyvinylethers, polyurethanes, styrene block copolymers, styrene/butadiene polymers, polyether block amide copolymers; ethylene/vinyl acetate copolymers, and vinyl acetate based adhesives,
   (ii) cellulose acetate butyrafe which is insoluble in water and substantially soluble in the adhesive carrier composition, and having a butyryl content of at least 30%, as a recrystallization inhibitor, and
   (iii) a therapeutically effective amount of one or more active agents.

2. The system according to claim 1, wherein the pressure-sensitive adhesive includes a hydroxy functional polyacrylate adhesive.

3. The system according to claim 1, wherein the cellulose acetate butyrate is present in an amount from about 0.5% to about 20%.

4. The system according to claim 1, wherein the pressure-sensitive adhesive carrier composition further includes one or more solvents and enhancers.

5. The system according to claim 1, wherein the one or more active agents is selected from the group consisting of steroidal hormones, analgesics, anti-inflammatory agents, central nervous system agents, cardioactive agents, anti-Parkinson's agents and anti-Alzhiemer's agents.

6. The system according to claim 5, wherein the steroidal hormone is selected from the group consisting of estradiol, ethinyl estradiol, progesterone, norethindrone, methyltestosterone and testosterone.

7. A method of suppressing recrystallization of active agents in an adhesive carrier composition of a transdermal drug delivery system during storage comprising:
   (a) preparing a pharmaceutically acceptable non-aqueous adhesive carrier composition comprising one or more active agents, and
   (b) mixing into the adhesive carrier composition a cellulose ester which is insoluble in water and substantially soluble in the adhesive carrier composition.

8. The method according to claim 7, wherein the adhesive carrier composition is a pressure-sensitive adhesive.

9. The method according to claim 8, wherein the pressure-sensitiVe adhesive includes a hydroxy functional polyacrylate adhesive.

10. The method according to claim 7, wherein the cellulose ester is selected from the group consisting of cellulose acetate butyrate, cellulose acetate propionate and cellulose acetate phthalate.

11. The method according to claim 7, wherein the cellulose ester is present in an amount from about 0.5% to about 20% by weight based on the dry weight of the total adhesive carrier composition.

12. The method according to claim 10, wherein the cellulose ester is cellulose acetate butyrate.

13. The method according to claim 7, wherein the one or more active agents is selected from the group consisting of steroidal hormones, analgesics, anti-inflammatory agents, central nervous system agents, cardioactive agents, anti-Parkinson's agents and anti-Alzhiemer's agents.

14. The method according to claim 13, wherein the steroidal hormone is selected from the group consisting of estradiol, ethinyl estradiol, progesterone, norethindrone, methyltestosterone and testosterone.

* * * * *

UNITED STATES PATENT AND TRADEMARK OFFICE
CERTIFICATE OF CORRECTION

PATENT NO. : 6,465,004 B1
DATED : October 15, 2002
INVENTOR(S) : Rossi-Montero et al.

It is certified that error appears in the above-identified patent and that said Letters Patent is hereby corrected as shown below:

Column 14,
Line 5, delete "butyrafe" and insert therefor -- butyrate --.

Signed and Sealed this

Thirty-first Day of August, 2004

JON W. DUDAS
*Director of the United States Patent and Trademark Office*